US008424522B2

(12) United States Patent
Sieber

(10) Patent No.: US 8,424,522 B2
(45) Date of Patent: Apr. 23, 2013

(54) METHOD FOR OPERATING A REBREATHER

(75) Inventor: Arne Sieber, Zell am See (AT)

(73) Assignee: DP Scandinavia AB, Vastra Frolunda (SE)

( * ) Notice: Subject to any disclaimer, the term of this patent is extended or adjusted under 35 U.S.C. 154(b) by 884 days.

(21) Appl. No.: 12/521,664

(22) PCT Filed: Dec. 27, 2007

(86) PCT No.: PCT/EP2007/064581

§ 371 (c)(1), (2), (4) Date: Aug. 19, 2009

(87) PCT Pub. No.: WO2008/080948

PCT Pub. Date: Jul. 10, 2008

(65) Prior Publication Data

US 2010/0313887 A1 Dec. 16, 2010

(30) Foreign Application Priority Data

Dec. 28, 2006 (AT) ........................... GM 899/2006 U

(51) Int. Cl.

| | |
|---|---|
| ***A61M 15/00*** | (2006.01) |
| ***A61M 16/00*** | (2006.01) |
| ***A62B 7/00*** | (2006.01) |
| ***A62B 9/00*** | (2006.01) |
| ***B63C 1/02*** | (2006.01) |
| ***F16K 31/02*** | (2006.01) |
| ***G05B 1/00*** | (2006.01) |

(52) U.S. Cl.
USPC ............ 128/204.22; 128/201.27; 128/203.14; 128/205.11

(58) Field of Classification Search ............. 128/200.24, 128/200.29, 201.21, 201.27, 202.22, 203.12, 128/203.14, 203.18, 203.25, 204.18, 204.21, 128/204.22, 204.29, 205.11, 205.12, 914; 405/185; 73/23.3
See application file for complete search history.

(56) References Cited

U.S. PATENT DOCUMENTS

| | | | | |
|---|---|---|---|---|
| 4,469,562 | A * | 9/1984 | Chang | 205/782.5 |
| 4,939,647 | A * | 7/1990 | Clough et al. | 128/201.27 |
| 5,542,284 | A | 8/1996 | Layzell et al. | |
| 6,712,071 | B1 * | 3/2004 | Parker | 128/204.21 |
| 2003/0127133 | A1 * | 7/2003 | Kim | 137/93 |
| 2004/0107965 | A1 * | 6/2004 | Hickle et al. | 128/204.22 |
| 2006/0201509 | A1 | 9/2006 | Forsyth et al. | |
| 2007/0215157 | A1 * | 9/2007 | Straw | 128/205.12 |
| 2011/0041848 | A1 * | 2/2011 | Stone et al. | 128/203.14 |
| 2011/0114094 | A1 * | 5/2011 | Stone et al. | 128/204.22 |

FOREIGN PATENT DOCUMENTS

| | | |
|---|---|---|
| GB | 2329343 | 3/1999 |
| GB | 2427366 | 12/2006 |

OTHER PUBLICATIONS

International search report in corresponding PCT/EP2007/064581.

* cited by examiner

*Primary Examiner* — Oren Ginsberg
(74) *Attorney, Agent, or Firm* — Young & Thompson

(57) ABSTRACT

The invention relates to a method for operating a rebreather, wherein oxygen is metered to the breathing gas as a function of a signal of at least one oxygen sensor (11). The oxygen sensor (11) is checked automatically by rinsing it with a gas having a known oxygen concentration. The safety of the system is improved in that the check is triggered automatically.

19 Claims, 2 Drawing Sheets

METHOD FOR OPERATING A REBREATHER

BACKGROUND OF THE INVENTION

1. Field of the Invention

The invention concerns a method for operating a rebreather, in which oxygen is metered to the breathing gas, wherein the oxygen content is monitored by at least one oxygen sensor and wherein the one oxygen sensor is tested by flushing with a gas with known oxygen concentration.

2. Description of the Related Art

Open-circuit diving apparatuses are characterized by a supply cylinder of breathing gas, which cylinder is filled with compressed air or another mix of breathing gas and a one-level or two-level pressure reducer, which reduces the pressure of the gas in the cylinder to ambient pressure. The exhaled air is emitted in the water, whereas only a small fraction of the oxygen in the breathing gas as well is really used. Thus at the water surface, about 3% of the inhaled gas is used (25 l breathing minute volume, 0.8 liter used oxygen, at rest), at a depth of for example 20 m, this value amounts due to the with 2 bar increased ambient pressure only a third, that is 1%. Consequently, for a diving operation at 20 m, 100 times more breathing gas must be carried along than what is actually used.

In order to avoid the low efficiency regarding breathing gas usage which is inherent in the system of open-circuit diving apparatuses (SCUBA, compressed air diving apparatuses), semi-closed circuit and fully-closed circuit rebreathers are employed. By these apparatuses, the breathing is done in a loop. The exhaled air is in these apparatuses cleaned from carbon dioxide by means of a carbon dioxide absorber and is again enriched with oxygen. Such apparatuses are further characterized by a one-part or two-part counterlung, which can receive the exhaled gas volumes. With rebreathers the efficiency regarding gas usage can be improved to up to 100%.

The present invention concerns such semi-closed circuit and fully-closed circuit rebreathers and a method for operating theses devices.

Whereas one by open-circuit diving apparatuses normally always inhales a gas with breathable oxygen content, is by semi-closed circuit rebreathers the $pO_2$ in the loop decided by the supplied amount of gas and the metabolism of the diver and is kept at a defined level in electronically controlled fully-closed circuit rebreathers by means of a control circuit (GB 24 045 93 A, U.S. 2003188744 A1, WO 2005/107390 A2). In manually controlled fully-closed circuit rebreathers is the oxygen supply manually set by the diver and thereby the oxygen partial pressure manually adjusted. The oxygen partial pressure of the breathing gas must be within defined limits to be breathable. Commonly is 0.16 bar considered as a lower limit and 1.6 bar as an upper limit. A $pO_2$ below or over these limits is classified as life threatening. Hence it is obvious, that a constant monitoring of the $pO_2$ is necessary for rebreathers. Fully-closed circuit rebreathers need $pO_2$ sensors for manual or electronically controlled adjustment of $pO_2$ in the loop. Normally electro-chemical sensors are employed as $pO_2$ sensors, which are calibrated with air or 100% $O_2$ before the diving operation at the water surface.

A correctly working $pO_2$ sensor for the application in rebreathers discloses an output signal (current or voltage), which is linearly dependent only on the $pO_2$ before the membrane of the sensor.

$pO_2$ sensors are very prone to errors. Typical errors which might occur are:

a) nonlinearity;

b) current limitation: in this case the $pO_2$ sensor becomes nonlinear above a certain $pO_2$ since the output current of the sensor (or the output voltage) due to an error can not rise over a certain level. This results in too low sensor signals for high $pO_2$;

c) erroneous signals from one or more sensors respectively the sensor signal processing;

d) erroneous calibration, $pO_2$ measuring equipments are, as already mentioned, calibrated at the water surface with air or 100% $O_2$ under normobaric conditions (at sea level therefore ~1000 mbar ambient pressure), whereby the sensitivity of the sensors is decided. The maximally reachable $pO_2$ is thus 1.0 bar. Since during diving operations there often is a $pO_2$ higher than 1.0 bar, it is important to test the sensors for a) and b). (Example for a calibration with 100% $O_2$: ambient pressure 1000 mbar, output voltage signal: 50 mV→sensitivity=50 mV/bar $pO_2$)

One tries to counter the error susceptibility of the $pO_2$ sensors by redundant use of $pO_2$ sensors. Hence normally three oxygen sensors are used in fully-closed circuit rebreathers. In case a sensor drops out, and thus its output signal differs from that of the other two, is this detected through a comparison between all three sensor signals with a "voting algorithm" (GB 240 45 93 A, WO 2004/112905 A1), and this sensor is no longer consulted for the adjustment of the $pO_2$.

In that way an erroneous sensor can be identified. This method however fails to work for the following errors:

e) drop-out of two sensors, which yet have the same output signal;

f) the same non-linearity for at least two sensors (>=two sensors from the same production batch, the same age, the same conditions . . . );

g) the same current limitation for at least two sensors.

Furthermore, for a detailed diving analysis, a continuous recording of all diving relevant data is necessary. Thus, depth profile, time and $pO_2$ are often stored in an internal memory of the $pO_2$ measuring equipment and can be transferred to a personal computer after the diving operation, wherein the resolution of time and the maximal length of the recording depends on the size of the memory and is thus limited.

Normally, special interface cables are needed for transfer to the personal computer. Especially for the efficient treatment of diving accidents, a fast analysis of the diving data is important. However, the fitting interface cable is often not available on the spot. The possibility to read such diving data without such a special cable with every commercially available pc is therefore desirable.

An object of the invention is therefore to develop a $pO_2$ measuring equipment in such a way, that errors in the $pO_2$ sensor signals, nonlinearities of the $pO_2$ sensor signals, a possible current limitation of $pO_2$ sensors are reliably detected and a detailed recording of the relevant diving data is made possible.

From U.S. Pat. No. 4,939,647 A a method is known, which at least partly solves the above-mentioned problems. Thereby an oxygen sensor is calibrated through flushing with pure oxygen. This makes a calibration at an oxygen partial pressure of 1 bar possible. However, it has turned out that such a calibration is not sufficient to reliably detect the above-mentioned errors.

BRIEF SUMMARY OF THE INVENTION

According to the invention, this task is solved by the test being automatically triggered. It is thus after a necessary and predefined calibration conducted a test, which however is not manually started, but instead automatically triggered. The test is hence independent of a possible stress situation, in which the diver is situated. In just such a stress situation however, because of an increased oxygen need and an increased breathing frequency, as well as the thereby connected increased production of $CO_2$, is the probability of the drop-out of a sensor increased. The test can according to setting, kind of abnormality etc lead to an alarm signal, trigger a switch to emergency operation or cause a correction of the calibration.

Preferably, the test is thereby done under water considering ambient pressure. Essential for the present invention is the fact, that the ambient pressure at the test also is decisive for the choice of moment for the test. In this way, the test can be carried out at an oxygen partial pressure, which is in the upper range of the normal measurement range. This means that especially the oxygen partial pressure is in the range of the upper limit of oxygen partial pressure, which for medical reasons can be tolerated for human beings. This means approximately that a diving depth of 6 m a flushing with pure oxygen is performed, at which the partial pressure is about 1.6 bar. The flushing is thereby done until a signal is reliably available, which signal corresponds to pure oxygen. As a general rule this needs four to six seconds.

Through this test of the first kind especially the linearity of the oxygen sensor and the function in the important range of higher oxygen partial pressure can be tested. This makes it possible to detect error sources which could not be detected by a calibration or test at land, since here the maximal oxygen partial pressure is limited to 1 bar. This test of the first kind is as a general rule done during the descent when the above-mentioned diving depth of about 6 m is reached. Thereafter further tests could continuously be done, that is tests of the second kind, which for example should detect if an oxygen sensor is affected in its function by condense water. Since these tests normally occur at larger diving depths, these are not carried out with pure oxygen, since otherwise unacceptable high partial pressures would be reached. The test is carried out with mixed gas, wherein here the oxygen partial pressure also can be quite below 1 bar.

The present invention further concerns a rebreather with at least one pressure cylinder for oxygen and a further pressure cylinder for a diluting gas and with a valve for supply of oxygen and/or diluting gas in the rebreathing loop, which valve is controlled as a function of the signal of at least one oxygen sensor, wherein a device for flushing of the oxygen sensor with a gas with known oxygen concentration is provided.

According to the invention, this rebreather is characterized by that the device is in connection with a pressure sensor and is controlled as a function of a signal of the pressure sensor in order to test the oxygen sensor The gas need for the test of the oxygen sensor can in particular be thereby minimized, that the comparison gas supply is arranged directly before the sensor membrane and in that way only the area before the membrane is flushed.

A slot for memory cards makes it possible, that diving relevant data are stored with a high time resolution and a personal computer with memory card slot is enough to read the data.

The measuring device is characterized by one or more integrated comparison gas supplies. A micro-controller with suitable software is thereby used for the signal processing, the calculations, the control of magnetic valves, presentation at the display and the storage of data in a memory card. When carried out as above, on one hand pure oxygen and the diluting gas used for fully-closed circuit rebreathers, respectively the supply gas used for semi-closed circuit rebreathers, are used as comparison gas. By means of a magnetic valve the comparison gases can be injected directly before the membrane of the oxygen sensors. The injection time amounts thereby preferably to between 5 and 10 seconds, according to the setting time for the oxygen sensors. In that way, the oxygen sensor measures, during the durance of the gas injection, only the oxygen partial pressure of the comparison gas, while the gas mix in the loop before the sensor is displaced by the comparison gas. From the depth, which normally is determined by a pressure sensor, the ambient pressure is calculated and together with the known oxygen content of the comparison gases, the actual oxygen partial pressure before the sensor membrane is calculated (desired value) and is compared to the actual value of the sensor (calculated from the sensor signal and the sensitivity determined at the calibration). Furthermore the maximal comparison mass flow is restricted to 1 to 2 bar l/min by integrated apertures.

It is hereby pointed out that the function of the rebreather apparatus is not affected during these tests and the diver can hence breathe fully normally. As well, the temporally supplied amount of oxygen during the test with 100% oxygen corresponds approximately to the human psychological oxygen consumption per time unit and should therefore not lead to an appreciable increase of the oxygen partial pressure in the loop.

In the tests described below a), b), c) and d) are automatically carried out by the µ-controller.

For test of the correct function of a $pO_2$ sensor the following methods are used:

At a defined time interval (for example every 2 min), the diluting gas for fully-closed circuit rebreathers or the supply gas for semi-closed circuit rebreathers is injected to the $pO_2$ measuring equipment before the membrane of the sensor by the µ-controller. Through the comparison of the desired value to the actual value, the $pO_2$ sensor can then be tested so that it works correctly. In the same way, the correct calibration can tested.

Linearity tests for semi-closed circuit rebreathers:

The $pO_2$ measuring equipment is calibrated with air or supply gas at the surface. At a defined time interval (for example every 2 min), the supply gas (known oxygen content) is injected to the $pO_2$ measuring equipment before the membrane of the sensor by the µ-controller. Through the comparison of the desired value to the actual value the $pO_2$ sensor can be tested for linearity.

Linearity tests for fully-closed circuit rebreathers:

The $pO_2$ measuring equipment is calibrated with 100% oxygen (1.0 bar $pO_2$) at the surface. In the beginning of the diving operation at a depth of preferably 5 m to 7 m is 100% oxygen injected before the membrane of the sensor by the µ-controller. The actual value of $pO_2$ for the gas before the sensor membrane is consequently 1.5 bar to 1.7 bar. A comparison with the actual sensor signal allows an evaluation of the linearity of the sensor. In principle also the oxygen valve of the control circuit can be used to flow the area before the sensors in order to in that way carry out an automatic linearity test. In this case, the diver should during the time for the test stop the breathing in order not to falsify the measurement result.

These linearity tests are also suitable to test the sensors for current limitation.

These test methods allow, as opposed to voting algorithm, a genuine test of an oxygen sensor during the diving operation. The errors a), b), c), d), e), f) and g) can be reliably detected. Especially, it is possible to test the sensors for a correct function during the whole diving operation at defined intervals.

In that way is in principle also the safe operation of a fully-closed circuit rebreather with only one oxygen sensor possible.

If the desired and actual values differ from each other, is the diver adverted by an alarm function. For fully-closed circuit rebreathers only $pO_2$ sensors are used for the adjustment, which sensors successfully have passed the automatic test of functions.

Due to condensation of water directly at the membrane of oxygen sensors (water droplets) error c) may occur. By means of the comparison gas volume flow such a water droplet can be blown away from the membrane. Thereafter the $pO_2$ sensor should again deliver correct values.

The invention is further characterized by an integrated memory card slot. Diving relevant data like sensor signals from one or more sensors, time, depth, and battery voltage are written once a second on a Secure Digital memory card (file system FAT 12, 16 or 32). A diving operation of 60 min corresponds to a data file with about 500 kilobytes. This data file can then be read by every personal computer, which is equipped with a commercially available reader/card slot for Secure Digital memory cards.

BRIEF DESCRIPTION OF THE DRAWINGS

Below the invention is closer explained in detail by means of the embodiments shown in the figures. They show.

DETAILED DESCRIPTION OF THE PREFERRED EMBODIMENTS

Figure 1:
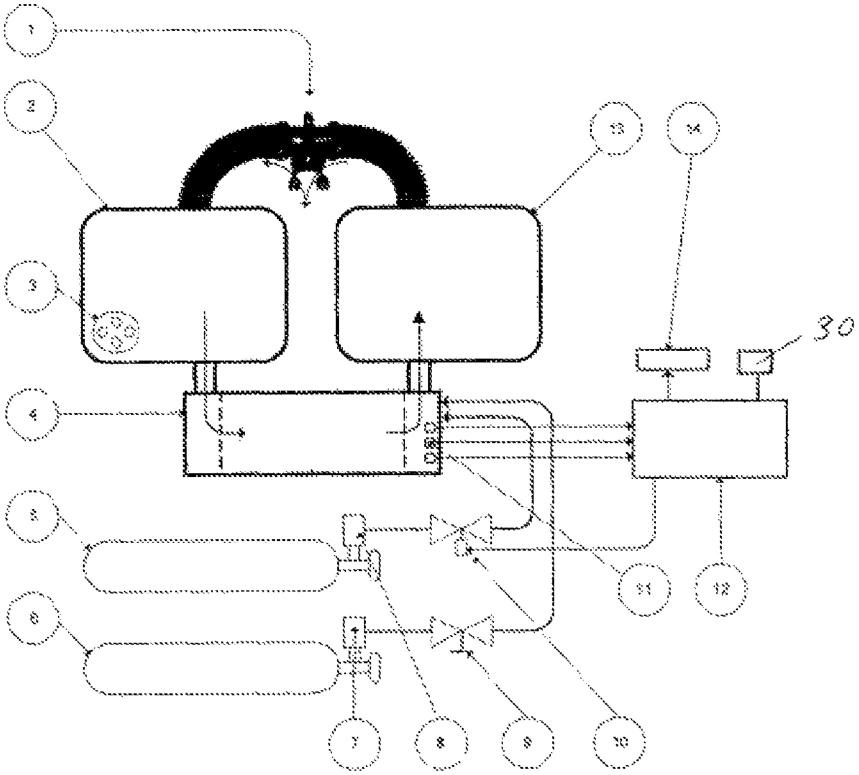
FIG. 1 the principal configuration of a rebreather according to the invention.

In FIG. 1 the principal configuration of a rebreather is illustrated. The diver exhales through the mouthpiece with directional valves 1 through the exhaling tube in the exhaling counter lung 2. Through the over-pressure valve 3 excessive gas can be released to the surroundings. The exhaled air is cleaned from carbon dioxide in the scrubber 4. The loop closes with the inhaling counterlung 13 and the inhaling tube. The oxygen sensors 11 are arranged in the scrubber. A μ-controller 12 calculates the $pO_2$ from the signals of the oxygen sensors and shows the diving relevant data on a display 14. In case the oxygen partial pressure $pO_2$ is too low in the loop, oxygen is supplied via the oxygen cylinder 5, the pressure reducer 8 and a magnetic valve 10. Furthermore diluting gas can be supplied to the loop via a lung automatic valve or a by-pass valve 9 from the diluting gas cylinder 6 and a further pressure reducer 7 (important during descent, when flushing the loop, or when blowing out the diver eyeglasses). The pressure reducers reduce the gas cylinder pressure to a pressure ~8-12 bar higher than the ambient pressure. Furthermore a pressure sensor 30 is used for determining the ambient pressure.

Figure 2:
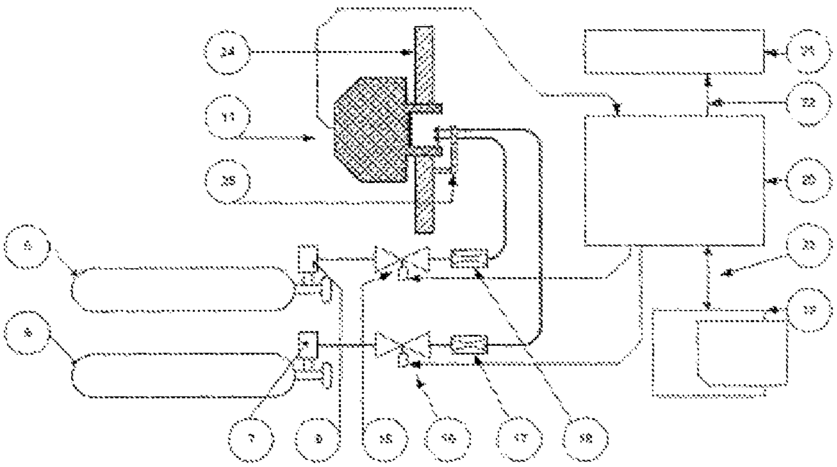
FIG. 2 an extended variant of an embodiment of the invention.

In FIG. 2 is the embodiment being an exemplary extension of the rebreather illustrated. The μ-controller 20 evaluates the signals of the oxygen sensor/sensors 11. These are screwed into a suspension 24 on the outlet side of the scrubber. Via a serial peripheral interface (short SPI) connection 22, a display 21 is connected. Via a further SPI connection 23, a memory card slot 19 for Secure Digital (short SD) cards is connected. If Compact Flash Cards are used, these are written on over a parallel connection instead of via a SPI connection. The μ-controller 20 can conduct 100% oxygen directly before the membrane of the $pO_2$ sensor/sensors via a magnet valve 10 from an oxygen cylinder 5 and a pressure reducer 8, whereby the flow rate (for example 1 bar l/min) is defined by an aperture 18. Furthermore, diluting gas with known oxygen content can be conducted before the membrane of the $pO_2$ sensor/sensors from the storage cylinder 6 via the pressure reducer 7 and a further magnet valve 16. Here as well, the maximal flow rate is defined by an aperture 17 (again for example 1 bar l/min)). The supply conducts are attached by means of a fixture 25 before the sensor membrane. It is further noted, that FIG. 2 is an extension of FIG. 1, i.e. the magnetic valve 10 and the manual valve 9 are furthermore still part of the loop.

The invention claimed is:

1. A method for operating a rebreather apparatus, in which oxygen is metered a breathing gas and an oxygen partial pressure is monitored by at least one oxygen sensor, the method comprising:

continuously and automatically testing the at least one oxygen sensor at defined intervals and at an ambient pressure determined by a pressure sensor by flushing the at least one oxygen sensor with a gas having a known oxygen concentration.

2. The method according to claim 1, wherein the testing occurs under water considering the ambient pressure.

3. The method according to claim 2, wherein the flushing occurs by direct injection of the gas with the known oxygen concentration before a membrane of the at least one oxygen sensor.

4. The method according to claim 2, wherein the testing is carried out as a function of the ambient pressure.

5. The method according to claim 1, wherein the flushing occurs by direct injection of the gas with the known oxygen concentration before a membrane of the at least one oxygen sensor.

6. The method according to claim 5, wherein the testing is carried out as a function of the ambient pressure.

7. The method according to claim 1, wherein the testing is carried out as a function of the ambient pressure.

8. The method according to claim 1, wherein a first test is carried out at a predefined ambient pressure by flushing with pure oxygen.

9. The method according to claim 8, wherein the first test is carried out at an ambient pressure, at which the oxygen partial pressure lies in an area of an upper limit of the oxygen partial pressure.

10. The method according to claim 9, wherein the first test is carried out at an ambient pressure, at which an oxygen partial pressure is in a range between 1.5 and 2 bar.

11. The method according to claim 1, wherein further testing is carried out at defined intervals by flushing with a diluting gas.

12. The method according to claim 1, wherein the testing occurs at defined intervals during which the rebreather apparatus is disposed at one or more depths under water.

13. A rebreather apparatus, comprising:

at least one first pressure cylinder for oxygen;

at least one second pressure cylinder for a diluting gas;

at least one valve to supply one or more of oxygen anddiluting gas in a rebreathing loop, the valve being controlled by a signal from at least one oxygen sensor; and a flushing device connected to and controlled by a pressure sensor, the flushing device, automatically at defined intervals, and at an ambient pressure determined by the pressure sensor, flushes the at least one oxygen sensor with a gas having a known oxygen concentration to test the at least one oxygen sensor.

14. The rebreather apparatus according to claim 13, wherein the at least one oxygen sensor has a membrane, at which a cleaning nozzle for flushing the at least one oxygen sensor with the gas with the known oxygen concentration is pointed.

15. The rebreather apparatus according to claim 14, further comprising a control device that triggers the flushing with oxygen when the defined ambient pressure is detected.

16. The rebreather apparatus according to claim 13, further comprising a control device that triggers the flushing with oxygen when the defined ambient pressure is detected.

17. The rebreather apparatus according to claim 16, wherein the control device has a memory card slot.

18. The rebreather apparatus according to claim 13, wherein an aperture is disposed in the rebreathing loop and reduces the flow rate of the gas.

19. The rebreather apparatus according to claim 13, wherein the flushing device flushes the at least one oxygen sensor automatically at defined intervals during which the rebreather apparatus is disposed at one or more depths under water.

* * * * *

UNITED STATES PATENT AND TRADEMARK OFFICE

CERTIFICATE OF CORRECTION

PATENT NO. : 8,424,522 B2
APPLICATION NO. : 12/521664
DATED : April 23, 2013
INVENTOR(S) : Arne Sieber It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 936 days.

Signed and Sealed this
Eighth Day of September, 2015

Michelle K. Lee
*Director of the United States Patent and Trademark Office*